United States Patent [19]

Beck et al.

[11] Patent Number: 4,808,604

[45] Date of Patent: Feb. 28, 1989

[54] N-(SUBSTITUTED PHENYL) TETRAZOL-5-YL CARBOXAMIDES AND ANTI-ALLERGIC USE THEREOF

[75] Inventors: Andreas Beck, Freiburg, Fed. Rep. of Germany; Alfred Sallmann, Bottmingen; Paul Wenk, Allschwil, both of Switzerland

[73] Assignee: Ciba-Geigy Corporation, Ardsley, N.Y.

[21] Appl. No.: 58,699

[22] Filed: Jun. 1, 1987

Related U.S. Application Data

[63] Continuation of Ser. No. 801,013, Nov. 22, 1985, abandoned.

[30] Foreign Application Priority Data

Oct. 3, 1985 [CH] Switzerland ............... 4288/85

[51] Int. Cl.$^4$ ............... C07D 257/04; A61K 31/41
[52] U.S. Cl. ............... 514/381; 548/251; 548/252
[58] Field of Search ............... 548/251, 252; 514/381

[56] References Cited

U.S. PATENT DOCUMENTS

| | | | |
|---|---|---|---|
| 3,966,965 | 6/1976 | Sellstedt | 424/309 |
| 4,119,783 | 10/1978 | Hall et al. | 560/43 |
| 4,159,278 | 6/1979 | Hall et al. | 260/501.15 |
| 4,442,115 | 4/1984 | Ramsden et al. | 424/269 |
| 4,448,729 | 5/1984 | Klaubert et al. | 548/254 |
| 4,507,498 | 3/1985 | Carson | 562/463 |

FOREIGN PATENT DOCUMENTS

| | | |
|---|---|---|
| 28063 | 5/1981 | European Pat. Off. . |
| 123541 | 10/1984 | European Pat. Off. . |
| 132367 | 1/1985 | European Pat. Off. . |
| 132366 | 1/1985 | European Pat. Off. . |
| 147973 | 7/1985 | European Pat. Off. . |
| 2006782 | 5/1979 | United Kingdom . |

Primary Examiner—David B. Springer
Attorney, Agent, or Firm—Irving M. Fishman

[57] ABSTRACT

Novel 4-acylresorcinol ethers of the formula

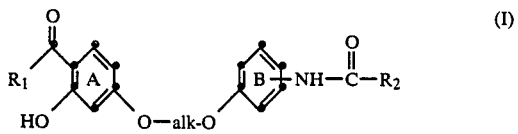

in which $R_1$ is lower alkyl, alk is a hydroxyalkylene radical which can be interrupted by oxygen and $R_2$ is 5-tetrazolyl, it being possible for the ring A to be additionally substituted by a lower alkyl, lower alkenyl, lower alkynyl, lower alkoxy and/or halogen and for the ring B to be additionally substituted by lower alkyl, lower alkanoyl, lower alkoxy, lower alkoxycarbonyl, carboxyl, cyano, carbamyl, halogen and/or trifluoromethyl, and salts thereof have antiallergic properties and can be used as active compounds for medicaments. They are prepared by methods known as per se.

10 Claims, No Drawings

N-(SUBSTITUTED PHENYL) TETRAZOL-5-YL CARBOXAMIDES AND ANTI-ALLERGIC USE THEREOF

This application is a continuation of application Ser. No. 801,013, filed Nov. 22, 1985, now abandoned.

The invention relates to novel 4-acylresorcinol ethers of the formula

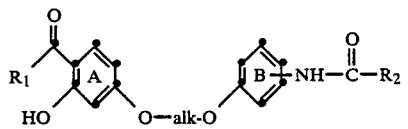

In which $R_1$ is lower alkyl, alk is ahydroxyalkylene radical which can be interrupted by oxygen and $R_2$ is 5-tetrazolyl, it being possible for the ring A to be additionally substituted by lower alkyl, lower alkenyl, lower alkynyl, lower alkoxy and/or halogen and for the ring B to be additionally substituted by lower alkyl, lower alkanoyl, lower alkoxy, lower alkoxycarbonyl, carboxyl, carbamyl, cyano, halogen and/or trifluoromethyl, and to salts thereof.

Examples of hydroxyalkylene radicals which can be interrupted by oxygen are hydroxy-lower alkylene radicals or hydroxy-(oxa)alkylene radicals or hydroxy-(dioxa)alkylene radicals, preferably linear radicals, in which the hydroxyl group is attached in a position higher than the α-position and lower than the ω-position in relation to the free valencies and in a position higher than the β-position in relation to (m) oxa member (s) which may be present, located in a position higher than the β-position and lower than the (ω−1)-position in relation to the free valencies. Radicals of this type are, in particular, radicals of the formula

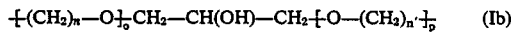

in which n and n' independently of one another are 2, 3 or 4 and o and p independently of one another are 0 or 1, in particular hydroxy-lower alkylene or hydroxy-(oxa)lower alkylene radicals of the formula Ib in which the indices o and p are 0 or one of the indices o and p is 1 and the other is 0 and n or n', respectively, is 2.

In the previous and following text, "lower" organic compounds and groups derived therefrom are to be understood, for example, as meaning groups having not more than 7, in particular not more than 4, carbon atoms (C atoms).

Lower alkyl is, for example, methyl, ethyl, propyl, isopropyl or butyl and also secondar or tertiary butyl, especially methyl in the case of $R_1$ and especially propyl in the case of a lower alkyl substituent in the ring A.

Lower alkoxy is, for example, methoxy, ethoxy, propoxy, isopropoxy or butoxy.

Halogen has, for example, an atomic number not higher than 53, in particular from 17 up to and including 53, and is, for example, fluorine, chlorine, bromine or iodine.

Lower alkenyl is, for example, allyl and also methallyl or but-4-enyl.

Lower alkynyl is, for example, propargyl.

Lower alkanoyl is, for example, formyl, acetyl, propionyl, butyryl, valeroyl or pivaloyl.

Hydroxy-lower alkylene in which the hydroxyl group is attached in a position higher than the α-position and lower than the ω-position is, for example, 1,3-(2-hydroxy)propylene, but can also be 1,4-(2-hydroxy)-butylene or 1,5-(3-hydroxy)-pentylene.

Hydroxy-(oxa)-lower alkylene in which the hydroxyl group is attached in a position higher than the α-position and lower than the ω-position in relation to the free valencies and in a position higher than the β-position in relation to the oxa member, which, in turn, is located in a position higher than the β-position and lower than the (ω−1)-position in relation to the free valences, is, for example, 1,7-(2-hydroxy-4-oxa)-heptylene, but can also be 1,6-(2-hydroxy-4-oxa)-hexylene.

Lower alkoxycarbonyl is, for example, methoxycarbonyl, ethoxycarbonyl, propoxycarbonyl, isopropoxycarbonyl or butoxycarbonyl.

Suitable salts of compounds of the formula I are preferably pharmaceutically acceptable salts, such as metal salts, ammonium salts or salts with organic bases. Examples of metal salts are appropriate alkali or alkaline earth metal salts, for example lithium, sodium, potassium, magnesium or calcium salts, and also pharmaceutically acceptable transition metal salts, such as zinc or copper salts. Salts with organic bases are formed, for example, by compounds of the formula I in which $R_2$ is carboxyl or 5-tetrazolyl, with monosubstituted, disubstituted or trisubstituted organic amines, such as appropriate alkylamines or hydroxyalkylamines, with suitable heterocyclic compounds containing at least one N atom, such as morpholine, thiomorpholine, piperidine or pyrrolidine, with amino-saccharides which can be N-substituted, for example with N-methyl-D-glucamine, or with basic amino acids, such as lysine, arginine, histidine or ornithine, those having the L-configuration being preferred. Examples of suitable alkylamines are mono-, di- or tri-lower alkylamines, such as ethylamine, tert.-butylamine, diethylamine, diisopropylamine, trimethylamine or triethylamine. Examples of suitable hydroxyalkylamines are mono-, di- or tri-hydroxyalkylamines, such as mono-, di- or tri-ethanolamine or diisopropanolamine, or hydroxy-lower alkyl-lower alkylamines, such as N,N-dimethylaminoethanol, N,N-diethylaminoethanol or tri-(hydroxymethyl)-methylamine.

Further salts which should be mentioned are pharmaceutically acceptable acid addition salts, such as hydrogen halides, methanesulfonates, N-cyclohexylsulfamates, maleates or fumarates of compounds of the formula I in which the radical $R_2$ is capable of forming appropriate salts.

The compounds of the formula I which have chiral C atoms can exist, depending on the number thereof, in forms which are mutually enantiomeric or diastereomeric or as mixtures thereof, such as mixtures of diastereomers, racemates or mixtures of racemates.

The compounds according to the invention are distinguished by valuable pharmacological properties. In particular they possess a pronounced antiallergic activity which can be deduced on the basis of a marked LTD$_4$-antagonism and a PAF-antagonism (PAF-acether antagonism, in vitro), since the compounds according to the invention inhibit contractions induced by LTD$_4$ in vitro within a range from about 0.005 to about 0.05 μmol/l. The LTD$_4$-antagonism can, for example, be demonstrated on an isolated guinea pig ileum. This is effected by recording the extent of contractions initiated by synthetic LTD$_4$ (leukotriene D$_4$, potassium salt) on ileum segments taken from guinea pigs having a body weight of 300 to 400 g and fastened in an organ bath in Tyrode solution (38° C., gassing with 95% $O_2$ and 5% $CO_2$) and loaded at 1p. The extent of the inhibition of these contractions attributable to the $LTD_4$-antagonistic action of test substance is measured. The concentration of the test substance, known as $IC_{50}$, which reduces contractions induced by $LTD_4$ to 50% of the initial value is determined. Examples of results obtained in this test arrangement were an $IC_{50}$ value of 0.0054 μmol/l for the triethanolammonium salt of N-{3-[3-(4-acetyl-3-hydroxy-2-propylphenoxy)-2-hydroxypropoxy]-4-bromo-6-methylphenyl}-1H-tetrazolyl-5-carboxamide and an $IC_{50}$ value of 0.03 μmol/l for the triethanolammonium salt of N-{3-[3-(4-acetyl-3-hydroxy-2-propylphenoxy)-2-hydroxypropoxy]2-cyanophenyl}-tetrazolyl-5-carboxamide and an $IC_{50}$ value of 0.087 μmol/l for ethyl N-{3-[3-(4-acetyl-3-hydroxy-2-propylphenoxy)-2-hydroxypropoxy]-phenyl}-oxamate and sodium N-{3-[3-(4-acetyl-3-hydroxy-2-propylphenoxy)-2-hydroxypropoxy]-2-cyanophenyl}-oxamate, both according to U.S. Pat. No. 4,448,729.

The $LTD_4$-antagonistic action of the new compounds can also be demonstrated in vivo by means of the inhibition of experimental $LTD_4$-induced bronchospasms in guinea pigs.

The invention relates primarily to compounds of the formula I in which $R_1$ is lower alkyl, alk is hydroxy-lower alkylene, hydroxy-(oxa)lower alkylene or hydroxy-(dioxa)lower alkylene in which the hydroxyl group is attached in a position higher than the α-position and lower than the ω-position in relation to the free valences and in a position higher than the β-position relative to (m) oxa member(s) which may be present, located in a position higher than the β-position and lower than the (ω−1)-position in relation to the free valences, and $R_2$ is 5-tetrazolyl, it being possible for the ring A to be additionally substituted by lower alkyl, lower alkenyl, lower alkynyl, lower alkoxy and/or halogen and for the radical B to be additionally substituted by lower alkyl, lower alkanoyl, lower alkoxy, lower alkoxycarbonyl, carbamyl, carboxyl, cyano, halogen and/or trifluoromethyl, and to salts thereof, in particular pharmaceutically acceptable salts.

The invention relates in particular to compounds of the formulae

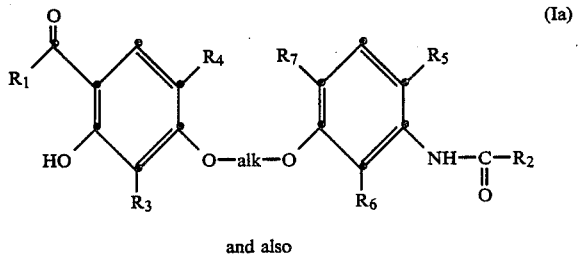

(Ia)

and also

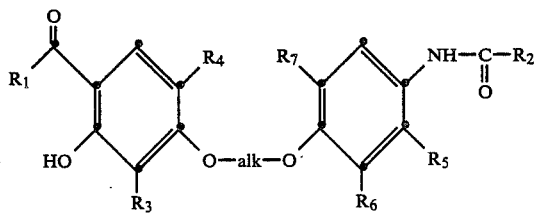

(Ib)

in which $R_1$ is lower alkyl having not more than 4 C atoms, such as methyl, $R_2$ is 5-tetrazolyl, $R_3$ is lower alkyl having not more than 4 C atoms, such as propyl, $R_4$ is hydrogen, lower alkyl having not more than 4 C atoms, such as methyl, lower alkoxy having not more than 4 C atoms, such as methoxy, or halogen having an atomic number of 35, such as chlorine or bromine, $R_5$ is hydrogen, lower alkyl having not more than 4 C atoms, such as methyl, halogen having an atomic number not higher than 35, such as chlorine or bromine, or trifluoromethyl, $R_6$ is hydrogen, lower alkyl having not more than 4 C atoms, such as methyl, lower alkoxy having not more than 4 C atoms, such as methoxy, cyano or halogen having an atomic number not higher than 35, such as chlorine or bromine, and $R_7$ is hydrogen, lower alkyl having not more than 4 C atoms, such as methyl, halogen having an atomic number not higher than 35, such as chlorine or bromine, lower alkoxycarbonyl having not more than 5 C atoms, such as ethoxycarbonyl, carboxyl, cyano or lower alkanoyl having not more than 7 C atoms, such as formyl, acetyl or pivaloyl, and alk is hydroxy-lower alkylene which has 3 or 4 C atoms and is, in particular, linear and linked to a terminal position, and in which the free valences emanate from C atoms in the β-position in relation to the hydroxyl group, such as 1,3-(2-hydroxy)-propylene, and to salts thereof, in particular pharmaceutically acceptable salts.

The invention relates first and foremost to compounds of the formula Ia in which $R_1$ is lower alkyl having not more than 4 C atoms, such as methyl, $R_3$ is linear lower alkyl having not more than 4 C atoms, such as propyl, $R_2$ is 5-tetrazolyl, $R_4$ is hydrogen, $R_5$ is lower alkyl having not more than 4 C atoms, such as methyl, $R_6$ is hydrogen, $R_7$ is halogen having an atomic number not higher than 35, such as chlorine or bromine, or cyano and alk is linear hydroxy-lower alkylene which has 3 or 4 C atoms and is linked at a terminal position and in which the free valency emanates from a C atom in the β-position relative to the hydroxyl group, such as 1,3-(2-hydroxy)-propylene, and to salts thereof, in particular pharmaceutically acceptable salts with bases.

The invention relates in particular to the compounds of the formula I mentioned in the examples and to salts thereof, especially phermaceutically acceptable salts, with bases.

The invention also relates to a process, based on methods known per se, for the preparation of compounds of the formula I and salts thereof. This process comprises (a) subjecting a compound of the formula

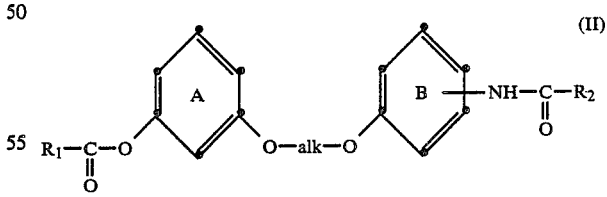

(II)

to a rearrangement or (b) reacting a compound of the formula

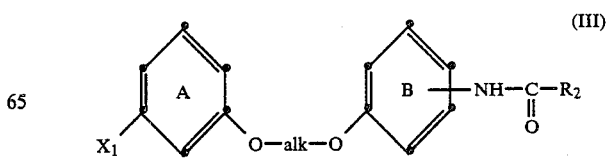

(III)

in which $X_1$ is free or etherified hydroxyl with a compound of the formula $R_1—X_2$ (IV) in which $X_2$ is free or functionally modified carboxyl, or (c) in a compound of the formula

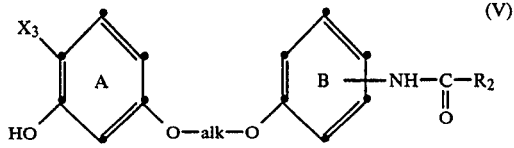
(V)

wherein $X_3$ is a radical which can be converted into the group of the formula $R_1—C(=O)—$, converting $X_3$ into this group, or (d) in a compound of the formula

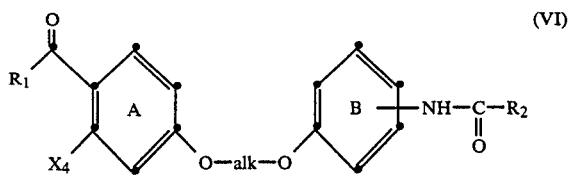
(VI)

in which $X_4$ is a radical which can be converted into hydroxyl, converting $X_4$ into hydroxyl, or (e) reacting with one another compounds of the formulae

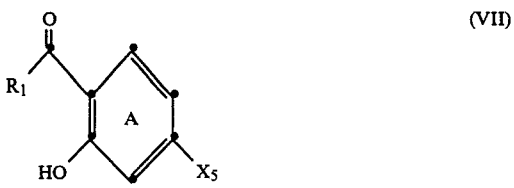
(VII)

and

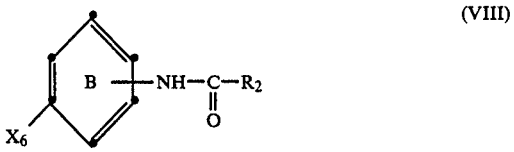
(VIII)

in which one of the radicals $X_5$ and $X_6$ is hydroxyl which may be in the salt form and the other is a hydroxyalkoxy radical which is substituted by a reactive, esterified hydroxyl group and may be interrupted by oxygen, or is an epoxyalkoxy radical which is interrupted by oxygen, or (f) in a compound of the formula

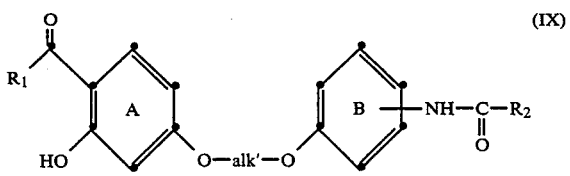
(IX)

in which alk' is a group which can be converted into a radical alk, converting alk' into a radical alk, or (g) reacting a compound of the formula

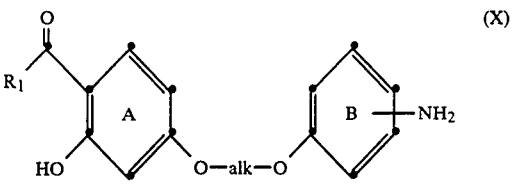
(X)

or a salt thereof, with a compound of the formula $$X_7—R_2 \qquad (XI)$$

in which $X_7$ is free or esterified or amidised carboxyl group or a carboxyl group in the form of the anhydride or a salt, or (h) in a compound of the formula

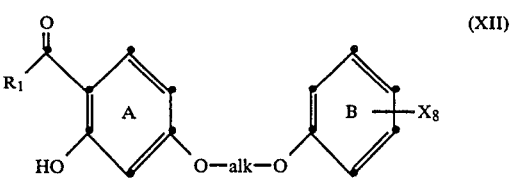
(XII)

in which $X_8$ is a radical which can be converted into the desired group of the formula $—NH—C(=O)—R_2$, converting $X_8$ into the latter and, if desired, converting a compound which can be obtained in accordance with the process into another compound of the formula I and/or converting a free compound which can be obtained in accordance with the process into a salt or converting a salt which can be obtained in accordance with the process into the free compound or into another salt.

Free or etherified hydroxyl $X_1$ in formula III is, for example, free hydroxyl or hydroxyl etherified with an aliphatic group, such as hydroxyl or lower alkoxy, for example methoxy, but can also be hydroxyl which is etherified with an araliphatic, cycloaliphatic or aromatic group, such as substituted or unsubstituted phenylalkoxy, for example benzyloxy, cycloalkoxy, for example cyclohexyloxy or cyclopentyloxy, or substituted or unsubstituted phenoxy.

Free or functionally modified carboxyl $X_2$ in formula IV is, for example, free or esterified carboxyl or carboxyl in the form of the anhydride, such as carboxyl, lower alkoxycarbonyl, halogencarbonyl or carboxyl in the form of the anhydride having the formula $—C(=O)—O—C(=O)—R_1$.

Radicals $X_3$ in formula V which can be converted into the group $R_1—C(=O)—$ are, for example, groups of formula $R_1—CH(X_9)—$ in which $X_9$ is hydrogen, free hydroxyl or hydroxyl which is esterified with an organic carboxylic acid, or groups of the formula $R_1—C(=NH)—$, and also free or functionally modified carboxyl groups, such as free carboxyl, carboxyl in the form of a salt or esterified carboxyl, or cyano. Hydroxyl which is esterified by an organic carboxylic acid is, for example, lower alkanoyloxy, such as acetoxy, but can also be substituted or unsubstituted benzyloxy. Examples of suitable salt forms of carboxyl $X_3$ are alkali metal, alkaline earth metal or ammonium salt forms, for example sodium or ammonium salt forms or halogenomagnesium salt forms. Esterified carboxyl $X_3$ is, for example, lower alkoxycarbonyl, but it can also be substituted or unsubstituted phenoxycarbonyl or phenyl-lower alkoxycarbonyl, such as benzyloxycarbonyl.

Examples of radicals $X_4$ which can be converted into hydroxyl in formula VI are etherified or esterified hydroxyl groups. Examples of suitable etherified hydroxyl $X_4$ are hydroxyl etherified with an aliphatic group, for example lower alkoxy, such as methoxy, or lower alkenyloxy, in particular lower alk-2-enyloxy, for example allyloxy, phenyl-lower alkoxy, in particular substituted or unsubstituted phenyl-lower alkoxy, such as benzyloxy, and also tetrahydropyran-2-yloxy or silyloxy, in particular tri-lower alkylsilyloxy, for example trimethylsilyloxy. Esterified hydroxyl $X_4$ is, for example, hydroxyl esterified with a carboxylic acid, such as an aliphatic or aromatic carboxylic acid, or with an aliphatic or aromatic half-ester of carbonic acid, such as lower alkanoyloxy, for example acetoxy, substituted or unsubstituted benzoyloxy, for example of the formula $R_1-C(=O)-O-$, lower alkoxycarbonyl which can be halogenated, for example methoxycarbonyl, ethoxycarbonyl, tertiary butoxycarbonyl, 2,2,2-triiodoethoxycarbonyl or 2,2,2-trichloroethoxycarbonyl, substituted or unsubstituted phenyl-lower alkoxycarbonyl, in particular 1-phenyl-lower alkoxycarbonyl, for example benzyloxycarbonyl, or substituted or unsubstituted phenoxycarbonyl.

Hydroxyl $X_5$ in formula VII or $X_6$ in formula VIII or carboxyl in formula XI, present in salt form, is present, in particular, in the form of an alkali metal salt, for example a sodium or potassium salt. Examples of hydroxyalkoxy radicals which can be interrupted by oxygen and substituted by reactive esterified hydroxyl groups, or of epoxyalkoxy radicals $X_5$ in formula VII or $X_6$ in formula VIII which can be interrupted by oxygenare expoxy-lower alkyl or epoxy(oxa)-lower alkyl radicals, in particular of the formula

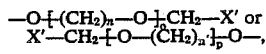

reactive, monoesterified dihydroxy-lower alkyl radicals in which the free hydroxyl group is attached in a position higher than the α-position in relation to the free valency and to the reactive esterified hydroxyl group, or corresponding reactive, monoesterified dihydroxy(mono)-alkyl or dihydroxy(dioxa)-alkyl radicals, in particular of the formula

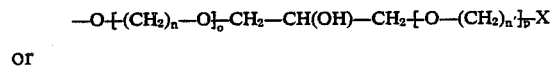

or

in which X is in each case reactive, esterified hydroxyl, X' is 1,2-epoxyethyl, n and n' are 2, 3 or 4, o is 0 or 1 and p is 0 or 1. Examples of reactive, esterified hydroxyl in this case are halogen, such as chlorine, bromine or iodine, or organic sulfonyloxy, such as lower alkanesulfonyloxy, for example methanesulfonyloxy, or substituted or unsubstituted benzenesulfonyloxy, for example benzenesulfonyloxy, p-bromobenzenesulfonyloxy or p-toluenesulfonyloxy. Preferably, n or n' is 2, o or p is 0 and p or o is 0 or, in the second place, 1.

Examples of radicals —alk'— which can be converted into radicals —alk— in formula IX are corresponding oxo-lower alkylene radicals or oxo-(monoox-a)-alkylene or oxo-(dioxa)-alkylene radicals, in particular of the formula

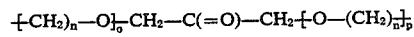

or etherified or esterified hydroxy-lower alkylene radicals or hydroxy-(monooxa)-alkylene or hydroxy-(dioxa)-alkylene radicals, in particular of the formula

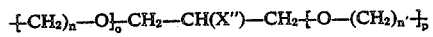

in which X" is etherified or esterified hydroxyl, n and n' are 2, 3 or 4, o is 0 or 1 and p is 0 or 1.

Etherified hydroxyl X" in this case is, for example, hydroxyl etherified with an α-aralkanol or a silanol, such as substituted or unsubstituted benzyloxy or tri-lower alkylsilyloxy, for example trimethylsilyloxy.

Esterified hydroxyl X" is, for example, hydroxyl esterified with a carboxylic acid, such as a lower alkanoic acid or a half-ester of carbonic acid, such as lower alkanoyloxy, for example acetoxy or pivaloyloxy, lower alkoxycarbonyloxy, for example tertiary butoxycarbonyloxy, or substituted or unsubstituted benzyloxycarbonyl, for example carbobenzoxy.

Examples of carboxyl $X_7$ which can be esterified, amidised or in anhydride form in formula XI are free carboxyl, esterified carboxyl $R_2$ or carboxyl esterified with a substituted or unsubstituted phenol, such as phenoxycarbonyl, 4-nitrophenoxycarbonyl or 2,4-dinitrophenoxycarbonyl, amidised carboxyl $R_2$ or activated carbamyl, such as 1-imidazolylcarbonyl or 1-(2,5-dimethylimidazolyl)-carbonyl, or carboxyl in the form of an anhydride with a hydrogen halide acid, such as halogencarbonyl, for example of the formula $Hal-C(=O)-$ in which Hal is chlorine, bromine or iodine, in particular chlorine.

Suitable starting materials XI are carboxyl groups, especially carboxyl groups in the form of a metal salt, for example potassium salt, or radicals of the formula $Hal-C(=O)-R_2$ (XIb). Examples of 5-tetrazolyl radicals present in a protected form are 1-( -aralkyl)-tetrazol-5-yl radicals which can be substituted in the aryl moiety, such as 1-benzyltetrazol-5-yl or 1-(p-methoxybenzyl)-tetrazol-5-yl.

A radical $X_8$ which can be converted into the group of the formula $-NH-C(=O)-R_2$ in formula XII is, for example, the group of the formula $-NH-C(=O)-CN$.

The performance of the reactions according to the process and the preparation of novel starting materials or intermediates are carried out analogously to the mode of reacting and forming known starting materials or intermediates. In this respect, even if not expressly mentioned below, use is made of the auxiliaries customary in each case, such as catalysts, condensation and solvolysis agents and/or solvents or diluents, and of the reaction conditions, such as temperature and pressure, and, if appropriate, protective gases which are customary in each case.

The rearrangement of compounds II in accordance with process variant (a) is effected, for example, photochemically or in the presence of an acid condensation agent, preferably in an inert solvent. Examples of suitable acid condensation agents are Lewis acids, in particular complex metal halides of the formula $M^nY_n$ (XIX) in which M is an n-valent, coordinatively unsaturated metal atom of group IIb, IIIa, IIIb, IVb, Va or VIIIb of the periodic table of the elements, for example a zinc$^{II}$, boron$^{III}$, aluminium$^{III}$, gallium$^{III}$, tin$^{IV}$, titanium$^{IV}$, antimony$^{V}$ or iron$^{III}$ atom, and Y is a halogen atom, in particular of atomic number not higher than 35, such as fluorine, chlorine or bromine. It is preferable to use boron trifluoride, aluminium trichloride, gallium chloride, tin tetrachloride or zinc chloride. Further suitable acid condensation agents are complex oxygen acids, in particular of sulfur or phosphorus, such as sulfuric acid, pyrosulfuric acid, phosphoric acid, pyrophosphoric acid or polyphosphoric acid. Examples of suitable inert solvents are carbon tetrachloride, tetrachloroethane, trichloroethylene, carbon disulfide or nitrobenzene. If necessary, the reaction is carried out with cooling or heating, for example at about −10° to about 40° C., in particular at +5° to +30° C.

Starting materials II can, for example, be prepared by reacting with one another in a customary manner compounds of the formulae

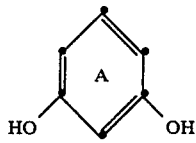

(XIII)

and

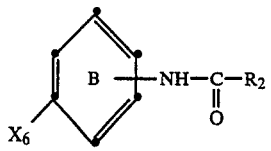

(VIII)

in which $X_6$ is a hydroxyalkyl radical which is substituted by reactive esterified hydroxyl and can be interrupted by oxygen or is an epoxyalkyl radical which can be interrupted by oxygen, for example a group of the formula

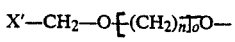

or

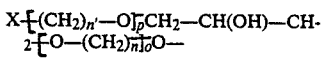

in which X is reactive esterified hydroxyl, for example halogen, and X' is epoxyethyl, and by O-acylating the reaction product of the formula

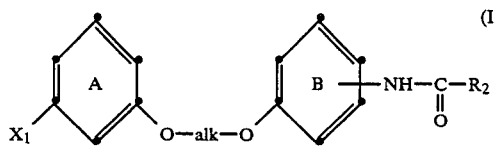

(III)

in which $X_1$ s hydroxyl, in a customary manner, for example by reacting it with a compound $R_1$—$X_2$ (IV) in which $X_2$ is, for example, halogenocarbonyl or carboxyl in the form of the anhydride of the formula —C(=O)—O—C(=O)—$R_1$. The preparation of compounds VIII is described under process variant (e).

The reaction of compounds III and IV in accordance with process variant (b) is usually effected in the presence of an acid condensation agent, advantageously in an inert solvent and, if necessary, with cooling or heating, for example at about −10° to +100° C., in particular at +5° to +65° C. Examples of suitable acid conden-sation agents and inert solvents are those indicated for process variant (a).

Starting materials III can, for example, be prepared by reacting with one another compounds of the formulae

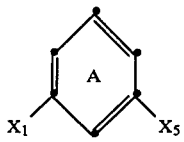

(XIV)

and

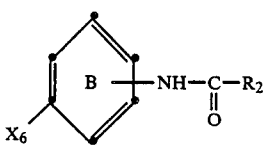

(VIII)

in which one of the radicals $X_5$ and $X_6$ is free hydroxyl or hydroxyl present in salt form and the other is a hydroxyalkyl radical which is substituted by reactive esterified hydroxyl and can be interrupted by oxygen or is an epoxyalkyl radical which can be interrupted by oxygen, for example a group of the formula

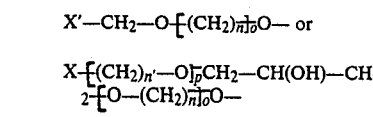

in which X is reactive esterified hydroxyl, for example halogen, and X' is epoxyethyl.

Starting materials IV are known.

The conversion of $X_3$ into a group $R_1$—C(=O)— in accordance with process variant (c) is effected in a customary manner, starting from compounds V in which $X_3$ is a group of the formula $R_1$—CH($X_9$)—, for example by oxidation, starting from compounds V in which $X_3$ is a group of the formula $R_1$—C(=NH)—, for example by solvolysis, and starting from compounds V, in which $X_3$ is free carboxyl or functionally modified carboxyl or carboxyl in the form of a salt, for example by reaction with a compound of the formula $R_1$—M (XV) in which M is a metal radical, for example of the formulae —M$^I$, —M$^{II}$/2 or M$^{II}$—hal, —M$^I$ is an alkali metal atom, for example lithium, M$^{II}$ is an alkaline earth metal or earth metal atom, for example magnesium, zinc or cadmium, and hal is a halogen atom, for example chlorine, bromine or iodine.

Examples of oxidising agents suitable for the oxidation of groups $X_3$ of the formula $R_1$—CH($X_9$)— are oxidising heavy metal compounds, such as Cr$^{III}$—, Cr$^{VI}$—, Mn$^{IV}$—, Mn$^{VII}$—, Fe$^{III}$—, Sn$^{IV}$— or V$^{V}$— compounds, for example chromium trioxide, potassium chromate or dichromate, manganesedioxide, potassium permanganate, iron trichloride, tin tetrachloride or vanadium pentoxide, and also oxidising oxygen acids of nitrogen, bismuth, selenium or the halogens or salts or anhydrides thereof, such as nitrogen dioxide, bismuth oxide, selenium dioxide, sodium hypochlorite, potassium chlorate or potassium periodate. Examples of oxidising agents particularly suitable for the oxidation of groups $X_3$ of the formula $R_1$—CH($X_9$)— in which $X_9$ is hydroxyl, are potassium permanganate in aqueous pyridine or aqueous acetone or pyridinium dichromate in methylene dichloride.

The solvolysis of groups $X_3$ of the formula $R_1$—C—(=NH)— is effected, in particular, by mild hydrolysis, i.e. the action of water, if necessary in the presence of a mild hydrolysis agent. Examples of the latter are proton acids, such as mineral acids, for example hydrochloric acid or sulfuric acid, or organic sulfonic or carboxylic acids, such as lower alkanesulfonic or substituted or unsubstituted benzenesulfonic acids or lower alkanoic acids, for example p-toluenesulfonic acid or acetic acid.

The reaction with a metal compound XV of compounds V in which $X_3$ is a free carboxyl group, a functionally modified carboxyl group or a carboxyl group present as a salt, is effected in a customary manner, for example in a dilower alkyl or alkylene ether, such as diethyl ether, tertiary butoxymethane, dioxane or tetrahydrofuran, if necessary with cooling or gentle warming, for example at $-60°$ to $+40°$ C., in particular at $-20°$ to $+25°$ C.

Starting materials V can, for example, be prepared by reacting with one another compounds of the formulae

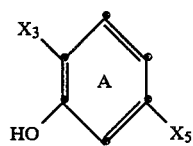
(XVI)

and

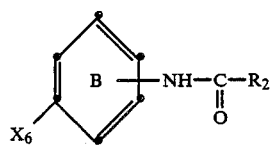
(VIII)

in which one of the radicals $X_5$ and $X_6$ is free hydroxyl or hydroxyl in salt form and the other is a hydroxyalkyl radical which is substituted by reactive esterified hydroxyl and which can be interrupted by oxygen or is an epoxyalkyl radical which can be interrupted by oxygen, for example a group of the formula

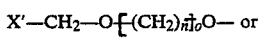   or

in which X is reactive esterified hydroxyl, for example halogen, and X' is epoxyethyl.

Starting materials V in which $X_3$ is a group $R_1$—CH—$(X_9)$— can also be prepared by reacting with one another compounds XVI ($X_3$=formyl) and VIII, and reacting the reaction product V ($X_3$=formyl) further with a metal compound XV.

Starting materials V in which $X_3$ is a group $R_1$—C(=NH)— can also be prepared by reacting, with a nitrile of the formula $R_1$—CN (XVII), a compound of the formula

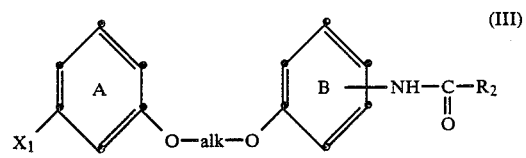
(III)

in which $X_1$ has the meaning indicated initially and is, for example, lower alkoxy, in the presence of a Lewis acid, for example a complex metal halide of the formula $M^n X_n$ (XIX) in which M, n and Y are as defined for process variant (a), in particular aluminium chloride. The intermediate V does not need to be isolated in this reaction; in general, it reacts further in accordance with the invention under the conditions of working up. This variant is particularly suitable for the preparation and further reaction of compounds V in which alk is a hydroxyalkylene radical which can be interrupted by oxygen.

The conversion of groups $X_4$ into hydroxyl in accordance with process variant (d) is effected in a customary manner, for example by treatment with a complex metal halide of the formula $M_n Y_n$ (XIX) in which M is an n-valent, coordinatively unsaturated metal cation of group IIa, IIb, IIIa, IIIb, Ivb, Va or VIIIb of the periodic table of the elements, for example a magnesium zinc$^{II}$, boron$^{III}$, aluminium$^{III}$, gallium$^{III}$, tin$^{IV}$, titanium$^{IV}$, antimony$^{V}$ or iron$^{III}$ or iron$^{VI}$ ion, and Y is a halogen atom of atomic number not higher than 35, such as fluorine or chlorine, for example aliminium trichloride, or with a tertiary organic ammonium salt, such as a pyridinium or tri-lower alkylammonium halide, for example pyridinium chloride or bromide or triethylammonium chloride, but can also be effected by solvolysis, in particular by hydrolysis, if necessary in the presence of a hydrolysis agent, preferably an acid hydrolysis agent. Hydrolysis agents are not only customary basic hydrolysis agents, such as alkali metal hydroxides, but also acid hydrolysis agents, for example mineral acids, for example hydrochloric, hydrobromic or hydriodic acid, sulfuric acid, phosphoric acid or polyphosphoric acid, and also complex metal acids, for example hexachloroantimonic acid, tetrafluoroboric acid and the like, and, in the case of hydroxyl groups $X_4$ esterified with organic carboxylic acids, also lower alkanoic acids, such as acetic acid. Examples of solvents in the hydrolysis are water-miscible organic solvents. It is preferable to carry out the reaction in each case in the presence of a solvent or diluent or a solubiliser, with cooling or heating, for example within a temperature range from about 0° to 120° C., and/or under an inert gas.

Thus, etherified hydroxyl groups can be split to form hydroxyl, for example by treatment with aqueous hydriodic acid, pyridinium chloride, for example in methylene dichloride, or hydrobromic acid in highly concentrated, for example 98%, acetic acid, or by treatment with boron tribromide or aluminium trichloride. In a modification of this process it is possible, for example, to treat compounds of the formulae

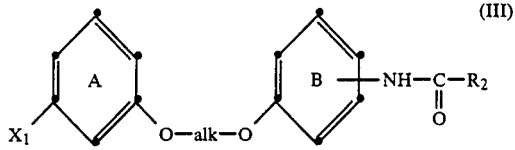

and

 (IV)

in which $X_1$ is etherified hydroxyl and $X_2$ is hydroxyl in the form of an anhydride, such as halogen or a group of the formula $R_1$—C(=O)—O—, with a Lewis acid, such as a complex metal halide of the formula $M^nY_n$ (XIX), for example aluminium trichloride, the hydroxyl group being liberated from the compound VI formed first in which $X_4$ is etherified hydroxyl. In another modification of this process variant it is possible to rearrange a compound VI in which $X_4$ is lower alk-2-enyloxy and the ring A is unsubstituted in the o-position in relation to $X_4$, by heating to about 150° to 250° C., preferably to about 190° to 220° C., advantageously in a solvent, such as diphenyl ether or N,N-dimethyl-N,N-diethylamine, to give a compound I in which the ring A is substituted by lower alk-2-enyl in the o-position in relation to the hydroxyl group.

In compounds VI containing, as group $X_4$, a substituted or unsubstituted α-phenyl-lower alkoxy group or another customary, protected hydroxyl group which can be cleaved by reduction, the hydroxyl group can advantageously be liberated by reduction. Thus reduction can be carried out, for example, by hydrogenation, i.e. by means of hydrogen in the presence of a hydrogenation catalyst, for example a palladium, platinum, nickel or rhodium catalyst, for example palladium-on-charcoal or Raney nickle.

Starting from compounds VI in which $X_4$ is hydroxyl esterified with an organic carboxylic acid, it is also possible to liberate the hydroxyl group by transesterification, i.e. by treatment with an alcohol, for example a lower alkanol, in the presence of an acid or basic agent, such as a mineral acid, for example sulfuric acid or an alkali metal hydroxide or alcoholate, for example sodium hydroxide or a sodium lower alkanolate.

Starting materials VI are prepared, for example, by reacting with one another compounds of the formulae

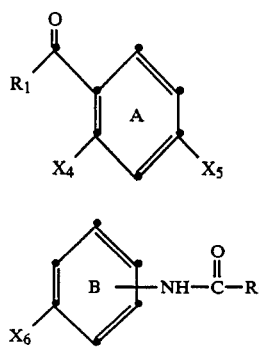

in which one of the radicals $X_5$ and $X_6$ is free hydroxyl or hydroxyl in the form of a salt and the other is a hydroxyalkyl radical which is substituted by reactive esterified hydroxyl and can be interrupted by oxygen, or is an epoxyalkyl radical which can be interrupted by oxygen, for example a group of the formula

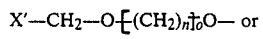

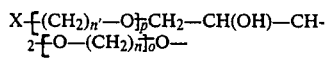

in which X is reactive esterified hydroxyl, for example halogen, and X' is epoxyethyl, or, for the preparation of compounds VI in which $X_4$ is etherified hydroxyl $X_1$, by reacting an appropriate compound of the formula

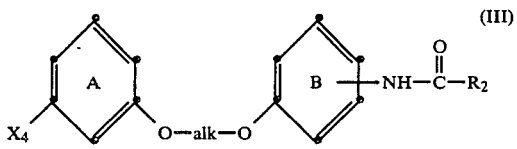

with a compound of the formula $R_1$—$X_2$ [IV, $X_2$=halogen-carbonyl or —O—C(=O)—$R_1$] under mild conditions, for example at $-10°$ to $+10°$ C. or using a Lewis acid having a mild action, for example zinc chloride or gallium chloride.

The reaction of compounds VII and VIII in accordance with process variant (e) is carried out in a customary manner, starting from starting materials in which $X_5$ or $X_6$ is a radical —O—alkH which is substituted by reactive esterified hydroxyl, for example in the presence of a basic condensation agent, such as a hydroxide or carbonate of an alkali or alkaline earth metal, such as sodium hydroxide, potassium hydroxide, potassium carbonate or calcium carbonate, advantageously in a lower alkanol, for example methanol or amyl alcohol, a di-lower alkyl ketone, for example acetone or diethyl ketone, or an N,N-di-lower alkyl-lower alkanoamide or an N-lower alkyl-lower alkanoic acid lactam, for example dimethylformamide or N-methylpyrrolidone.

The starting materials VII are prepared, for example, by reacting a compound of the formula

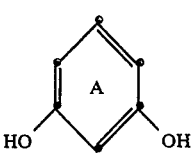

in the presence of a Lewis acid, for example aluminium trichloride or zinc chloride, with a compound of the formula $R_1$—$X_2$ [IV; $X_2$=halogenocarbonyl or —O—C(=O)—$R_1$], and, if desired, in the resulting compound VII in which $X_5$ is hydroxyl, by converting the hydroxyl group in the p-position relative to $R_1$—C(=O)— into a hydroxyalkoxy or epoxyalkoxy radical which is substituted by halogen and can be interrupted by oxygen, by reaction with, respectively, a dihalogenoalkanol or halogenoalkane epoxide which can be interrupted by oxygen.

Compounds VIII can be obtained, for example, by reducing the nitro group in a compound of the formula

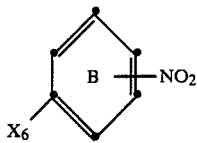

(XX)

to give amino, for example by means of hydrogen in the presence of Raney nickel, and by reacting the compound of the formula

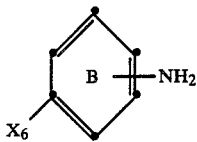

(XXI)

in the presence of a base, for example triethylamine or pyridine, with a compound of the formula Hal—C(=O)—R$_2$ (XIb; Hal=halogen), and, if desired, in the resulting compound VII in which X$_5$ is hydroxyl, by converting the hydroxyl group in the p-position relative to R$_1$—C(=O)— into a hydroxyalkoxy or epoxyalkoxy radical which is substituted by halogen and can be interrupted by oxygen, by reaction with, respectively, a dihalogenoalkanol or halogenoalkane epoxide which can be interrupted by oxygen.

The conversion of hydroxyl X$_5$ or X$_6$ into a hydroxyalkoxy radical which is substituted by reactive esterified hydroxyl and which can be interrupted by oxygen or into an epoxyalkyl radical which can be interrupted by oxygen can also be carried out in stages in each case. Thus a compound VII or VIII containing a free hydroxyl group X$_5$ or X$_6$ can first be reacted with a compound of the formula X—(CH$_2$)$_n$—OH (XXII) to give the corresponding compound VII or VIII, respectively, in which X$_5$ or X$_6$ is a group of the formula

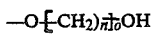

and o is 1. This intermediate can then be reacted (a) with a compound of the formula X—CH$_2$—X′ (XXIV) or (b) first with a compound XXIV and then with a compound XXII in order to obtain a corresponding compound VII or VIII in which X$_5$ or X$_6$ is a group of the formulae

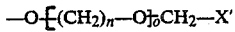 (a)

or

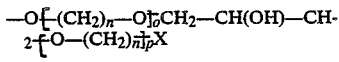 (b)

in which o and p are 1.

It is also possible, however, to carry out the reaction with a compound of the formula X—CH$_2$—CH(X″)—CH$_2$X (XXV) in which X is reactive esterified hydroxyl, such as chlorine, bromine or iodine, and X″ is hydroxyl esterified with a carboxylic acid, such as lower alkanoyloxy, for example acetoxy, to give a compound VII or VIII in which X$_5$ or X$_6$, respectively, is a group of the formula —CH$_2$—CH(X″)—CH$_2$X, and to convert this group into a group of the formula —CH$_2$—X′ by treatment with an alkali metal hydroxide, for example sodium hydroxide in methanol.

The conversion of the radical alk′ of a compound IX in accordance with process variant (f) is carried out in a customary manner, for example by reduction, starting from compounds IX in which alk′ is an alkylene radical substituted by oxo or by hydroxyl etherified with an α-alkanol or by hydroxyl esterified with a carboxylic acid mono-α-aralkyl radical, and by solvolysis, starting from compounds IX in which alk′ is a radical alk which is substituted by other etherified or esterified hydroxyl groups than those mentioned above.

Examples of suitable reducing agents for the reduction of radicals alk′ substituted by oxo to give the corresponding radicals alk are alkali metal borohydrides, such as lithium borohydride, sodium borohydride or sodium cyanoborohydride, or secondary alcohols, such as secondary lower alkanols or cyclo-lower alkanols, for example isopropanol or cyclohexanol, in the presence of an aluminium alcoholate, in particular isopropanol in the presence of aluminium isopropanolate. The reaction with the alkali metal borohydrides mentioned is advantageously carried out in a lower alkanol, a di-lower alkyl ether or lower alkylene ether or mixtures of these solvents, for example in ethanol. The reaction with alcohols in the presence of an aluminium alcoholate is advantageously carried out in an excess of the alcohol used as the reducing agent.

The reductive cleavage of α-aralkoxy or α-aralkoxycarbonyloxy to give hydroxyl is preferably carried out by hydrogenolysis, i.e. the action of hydrogen in the presence of a hydrogenation catalyst, such as a palladium, platinum, iridium or nickel catalyst, for example palladium-on-charcoal, platinum oxide or Raney nickel, advantageously in a lower alkanol, for example in methanolic solution, and, if necessary, under an excess pressure and/or with heating, for example at about 1 to 10 bar and 20° to 60° C.

The solvolytic liberation of hydroxyl from other etherified or esterified hydroxyl groups than those mentioned above, such as silyloxy, lower alkanoyloxy or lower alkoxycarbonyloxy, is effected, for example, by hydrolysis (reaction with water), alcoholysis (reaction with an alcohol) or ammonolysis/aminolysis (reaction with ammonia or an amine containing at least one free hydrogen), if necessary in the presence of an acid or basic agent and/or with heating, for example at about 20° to 100° C. Examples of suitable acid agents are mineral acids, such as hydrohalic acids, for example hydrochloric acid, or oxygen acids of sulfur or phosphorus, for example sulfuric or phosphoric acid, or organic sulfonic or carboxylic acids, such as lower alkanesulfonic acids or substituted or unsubstituted benzene sulfonic acids or lower alkanoic acids, for example p-toluenesulfonic acid or acetic acid. Examples of basic hydrolysis agents are hydroxides or carbonates of alkali metals, for example potassium carbonate, sodium hydroxide or potassium hydroxide, and, for the alcoholysis, corresponding alcoholates, such as alkali metal lower alkanolates, for example sodium methanolate.

Starting materials IX can be obtained, for example, by reacting with one another compounds of the formulae

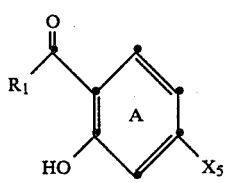

(VII)

-continued

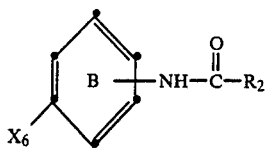
(VIII)

in which one of the radicals $X_5$ and $X_6$ is free hydroxyl or hydroxyl in the form of a salt and the other is a radical —O—alk'—X containing a reactive esterified hydroxyl X, i.e. an alkoxy radical which is substituted by reactive esterified hydroxyl and additionally by oxo or etherified or esterified hydroxyl and which can also be interrupted by oxygen. This radical has, for example, one of the formulae

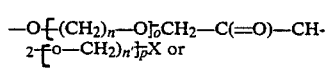

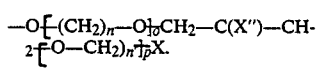

The reaction of the corresponding compounds VII and VIII and the preparation thereof is carried out, for example, in a manner analogous to that indicated for process variant (e).

The reaction of compounds X and XI in accordance with process variant (g) can be carried out in a customary manner, in particular in the manner known from the literature for analogous reactions, if necessary in the presence of a condensation agent, for example in the reaction with a free 5-halogenocarbonyltetrazole or a 5-halogenocarbonyltetrazole which is protected in the 1-position, a basic condensation agent, such as a tertiary organic nitrogen base, for example triethylamine or pyridine.

5-halogenocarbonyltetrazoles protected in the 1-position are preferably prepared in situ by reacting an alkali metal hydroxide or carbonate, for example sodium or potassium hydroxide, for example by reacting an alkali metal salt, for example the potassium salt, of a free tetrazol-5-carboxylic acid or tetrazol-5-carboxylic acid which is protected in the 1-position with oxalylchloride in the presence of pyridine.

The 1-protective group of 5-tetrazolyl radicals $R_2$ can subsequently be split off, for example by treatment with trifluoroacetic acid/anisole or by hydrogenolysis, in particular by means of hydrogen and palladium-on-charcoal.

Starting materials X can be prepared, for example, by reacting with one another compounds of the formulae

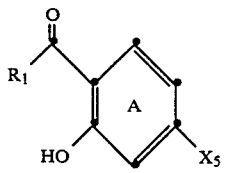
(VII)

and

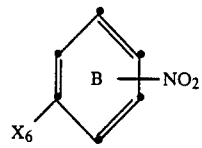
(XX)

in which one of the radicals $X_5$ and $X_6$ is free hydroxyl or hydroxyl in the form of a salt and the other is a hydoxyalkyl radical which is substituted by reactive esterified hydroxyl and which can be interrupted by oxygen, or is an epoxyalkyl radical which can be interrupted by oxygen, for example a group of the formula

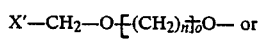

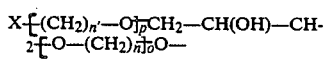

respectively, in which X is reactive esterified hydroxyl, for example halogen, and X' is epoxyethyl, and, in the resulting compound of the formula

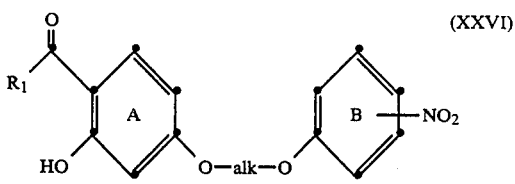
(XXVI)

reducing the nitro group to amino, for example by reaction with hydrogen in the presence of a hydrogenation catalyst, such as palladium-on-charcoal or, in particular, Raney nickel, for example in tetrahydrofuran.

The conversion of the group $X_8$ in compounds XII into groups of the formula —NH—C(=O)—$R_2$ in accordance with process variant (h) is effected, for example, by reaction with hydrazoic acid.

The reaction of groups $X_8$ of the formula —NH—C(=O)—CN with hydrazoic acid is preferably effected by forming the latter in situ by treating an alkali metal azide with an acid, such as hydrochloric acid, preferably in toluene or similar solvents.

The starting materials XII are prepared, for example, by reacting a compound of the formula

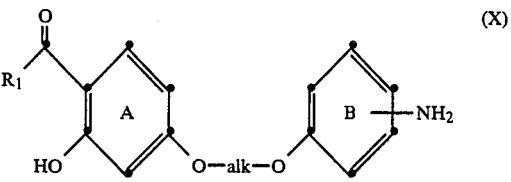
(X)

or an acid addition salt thereof with cyanoformic acid of formula NC—COOH (XXVIIa) or a derivative, preferably a functional derivative, thereof. Functional derivatives of acids XXVIIa are, in particular, acid derivatives containing an esterified carboxyl group or a carboxyl group in anhydride form, such as lower alkoxycarbonll or halogenocarbonyl, for example chlorocarbonyl or bromocarbonyl. Examples of functional derivatives of acids XXVIIa which may be mentioned are cyanoformyl chloride or cyanogen.

The reaction of compounds X with acids XXVIIa or derivatives thereof can be carried out in a customary manner, for example in the presence of a water-binding agent, such as an acid anhydride, for example phosphorus pentoxide or dicyclohexylcarbodiimdie, or a condensation agent, for example an acid or basic condensation agent, such as a mineral acid, for example hydrochloric acid, or an alkali metal hydroxide or carbonate, for example sodium hydroxide or potassium hydroxide, or an organic nitrogen base, for example triethylamine or pyridine. It is preferable to use an organic nitrogen base as condensation agent 1 in the reaction with an acid anhydride, such as an acid chloride. The reaction with carboxylic acid is preferably carried out in the presence of a water-binding agent. If necessary, the reaction is carried out in each case in an inert solvent, at normal temperature or with cooling or warming, for example within a temperature range from about 0° to about 100° C., in a closed vessel and/or under an inert gas, for example nitrogen.

A compound of the general formula I which can be obtained in accordance with the invention can be converted in a manner known per se into another compound of the general formula I.

Thus, for example, a free carboxyl group can be converted into lower alkoxycarbonyl in a customary manner, for example by treatment with a diazo-lower alkane or a tri-lower alkyloxonium, tri-lower alkylcarboxonium or di-lower alkylcarbonium salt, such as a hexachloroantimonate or hexafluorophosphate, or, in particular, by reaction with a lower alkanol or a reactive derivative, such as a carboxylic, phosphorous, sulfurous or carbonic acid ester thereof, for example a lower alkanecarboxylic acid ester, tri-lower alkyl phosphite or di-lower alkyl sulfite, or can be converted into carbamyl or cyano by reaction with ammonia, dehydration of the ammonium salt form first formed and, if desired, the carbamyl group.

Lower alkoxycarbonyl, carbamyl or cyano can be hydrolysed to give the free carboxyl group in a customary manner, for example by hydrolysis in the presence of a catalyst, for example a basic or acid agent, such as a strong base, for example sodium hydroxide or potassium hydroxide, or a mineral acid, for example hydrochloric acid, sulfuric acid or phosphoric acid.

It is also possible to introduce substituents into the phenyl ring A and/or B and/or to convert existing substituents into other substituents in a compound which can be obtained in accordance with the invention. Thus it is possible to introduce lower alkyl into the ring A and/or B or to introduce lower alkanoyl into the ring B by reaction with a lower alkylhalide or lower alkene or a lower alkanoic acid halide or anhydride, in each case in the presence of a Lewis acid, such as aluminium trichloride. It is also possible to introduce halogen, for example by treatment with a halogen in the presence of a Lewis acid, such as iron-III chloride, or by reaction with N-chlorosuccinimide. It is also possible to reduce lower alkenyl or lower alkynyl radicals to lower alkyl, for example by treatment with hydrogen in the presence of a hydrogenation catalyst, for example palladium-on-charcoal. Furthermore, halogen, in particular iodine, can be replaced by trifluoromethyl by reaction with trifluoroiodomethane in the presence of copper, or by cyano by reaction with an alkali metal cyanide.

Depending on the choice of starting materials and procedures, the novel compounds can exist in the form of one of the possible isomers or as a mixture thereof, for example, depending on the number of asymmetric carbon atoms, as pure optical isomers, such as antipodes, or as mixtures of isomers, such as racemates, mixtures of diastereoisomers or mixtures of racemates.

Resulting mixtures of diastereomers and mixtures of racemates can, by virtue of the physicochemical differences between the constituents, be separated into the pure isomers, diastereomers or racemates in a known manner, for example by chromatography and/or fractional crystallisation.

Resulting racemates can also be resolved into the optical antipodes by known methods, for example by recrystallisation from an optically active solvent, by means of microorganisms or by reacting an acid end product with an optically active base which forms salts with the racemic acid and separating the salts obtained in this manner, for example on the basis of their differing solubilities, into the diastereomers, from which the antipodes can be liberated by the action of suitable agents. It is advantageous to isolate the more active of the two antipodes.

Resulting free compounds of the formula I, for example those in which $R_2$ represents carboxyl, can be converted into salts in a manner known per se, for example by treatment with a base or with a suitable salt of a carboxylic acid, usually in the presence of a solvent or diluent.

Resulting salts can be converted into the free compounds in a manner known per se, for example by treatment with an acid reagent, such as a mineral acid.

The compounds, including their salts, can also be obtained in the form of their hydrates or can include the solvent used for crystallisation.

Because of the close relationship between the novel compounds in the free form and in the form of their salts, what is stated in this specification in respect of the free compounds or the salts thereof also applies by analogy to the corresponding salts and free compounds.

The invention also relates to those embodiments of the process in which a compound obtainable at any stage of the process as an intermediate is used as the starting material and the missing stages are carried out, or a starting material is used in the form of a salt and/or racemate or antipodes, or, in particular, is formed under the reaction conditions.

The novel starting materials and intermediates formed in the processes according to the invention and their preliminary stages also form a subject of the invention.

It is preferable to use such starting materials and to select the reaction conditions in such a way as to obtain the compounds listed above as particularly preferred.

The present invention also relates to pharmaceutical formulations containing one of the compounds, according to the invention, of the formula I or a pharmaceutically acceptable salt thereof. The pharmaceutical formulations according to the invention are formulations which are intended for topical and local application and for enteral, such as oral or rectal, administration and also parenteral administration to warm-blooded animals and for inhalation by the latter, and which contain the pharmacological active compound on its own or together with a pharmaceutically acceptable excipient. The dosage of the active compound depends on the species of warm-blooded animal, its age and individual condition and on the mode of administration.

The novel pharmaceutical formulations contain, for example, from about 10% to about 95%, preferably from about 20% to about 90%, of the active compound.

Examples of pharmaceutical formulations according to the invention are formulations in aerosol or spray form or in dosage unit forms, such as coated tablets, tablets, capsules or suppositories, and also ampoules.

The pharmaceutical formulations of the present invention are prepared in a manner known per se, for example by means of conventional mixing, granulating, coating, dissolving or lyophilising processes. Thus pharmaceutical formulations for oral administration can be obtained by combining the active compound with solid excipients, if appropriate granulating a resulting mixture, and processing the mixture or granules to give tablets or coated tablet cores, if desired or necessary, after the addition of suitable adjuncts.

Suitable excipients are, in particular, fillers, such as sugars, for example lactose, sucrose, mannitol or sorbitol, cellulose preparations and/or calcium phosphates, for example tricalcium phosphate or calcium hydrogenphosphate, and also binders, such as starch pastes, for example maize, wheat, rice or potato starch pastes, gelatine, tragacanth, methylcellulose and/or polyvinylpyrrolidone, and/or, if desired, disintegrators, such as the starches mentioned above, and also carboxymethylstarch, cross-linked polyvinylpyrrolidone, agar or alginic acid or a salt thereof, such as sodium alginate. Adjuncts are primarily glidants and lubricants, for example silica, talc, stearic acid or salts thereof, such as magnesium stearate or calcium stearate, and or polyethylene glycol. Coated tablet cores are provided with suitable coatings, if appropriate coatings resistant to gastric juices, use being made, inter alia, of concentrated sugar solutions which can contain gum arabic, talc, polyvinylpyrrolidones, polyethylene glycol and/or titanium dioxide, solutions of lacquers in suitable organic solvents or solvent mixtures or, for the preparation of coatings resistant to gastric juices, solutions of suitable cellulose preparations, such as acetylcellulose phthalate or hydroxypropylmethylcellulose phthalate. Dyestuffs or pigments can be added to the tablets or tablet coatings, for example in order to identify or characterise different doses of active compound.

Further pharmaceutical formulations which can be administered orally are dry-filled capsules made of gelatine and also soft, closed capsules made of gelatine and a plasticiser, such as glycerol or sorbitol. The dry-filled capsules can contain the active compound in the form of granules, for example mixed with fillers, such as lactose, binders, such as starches, and/or lubricants, such as talc or magnesium stearate, and, if necessary, stabilisers. In soft capsules the active compound is preferably dissolved or suspended in suitable liquids, such as fatty oils, paraffin oil or liquid polyethylene glycols, and stabilisers can also be added.

Examples of pharmaceutical formulations suitable for rectal administration are suppositories consisting of a combination of the active compound and a suppository base. Examples of suitable suppository bases are natural or synthetic triglycerides, paraffin hydrocarbons, polyethylene glycols or higher alkanols. It is also possible to use gelatine rectal capsules containing a combination of the active compound and a base; examples of suitable bases are liquid triglycerides, polyethylene glycols or paraffin hydrocarbons.

Formulations suitable for parenteral administration are primarily aqueous solutions of an active compound in a water-soluble form, for example a water-soluble salt, and also suspensions of the active compound, such as appropriate oily injection suspensions, use being made of suitable lipophilic solvents or vehicles, such as fatty oils, for example sesame oil, or synthetic fatty acid esters, for example ethyloleate or triglycerides, or aqueous injection suspensions containing substances which increase the viscosity, for example sodium carboxymethylcellulose, sorbitol and/or dextran and, if appropriate, also stabilisers.

Examples of inhalation formulations for the treatment of the respiratory passages by nasal or buccal administration are aerosols or sprays which can distribute the pharmacological active compound in the form of a powder or in the form of drops of a solution or suspension. Formulations having powder-distributing properties usually contain, besides the active compound, a liquid propellant gas having a boiling point below room temperature and, if desired, excipients such as liquid or solid, non-ionic or anionic surface-active agents and/or diluents. Formulations in which the pharmacological active compounds is present in solution contain, in addition to the latter, a suitable propellant and also, if necessary, an additional solvent and/or a stabiliser. Instead of the propellant gas, it is also possible to use compressed air, it being possible to generate the latter, as required, by means of a suitable compression and expansion device.

Examples of pharmaceutical formulations for topical and local application are lotions and creams for the treatment of the skin, which contain a liquid or semi-solid oil-in-water or water-in-oil emulsion, and ointments (preferably containing a preservative), eye drops for the treatment of the eyes, which contain the active compound in an aqueous or oily solution, and eye ointments which are preferably prepared in a sterile form, powders, aerosols are sprays for the treatment of the nose (similar to those described above for the treatment of the respiratory passages), and coarse powders administered by rapid inhalation through the nasal orifices and nasal drops which contain the active compound in an aqueous or oily solution, or lozenges for local treatment of the mouth, which contain the active compound in a composition which is generally prepared from sugar and gum arabic or tragacanth and to which flavourings can be added, and also pastilles which contain the active compound in an inert composiion, for example a composition composed of gelatine and glycerol or sugar and gum arabic.

The invention also relates to the use of the novel compounds of the formula I and salts thereof as pharmacologically active compounds, in particular as an antiallergic agent, preferably in the form of pharmaceutical formulations. The daily dose which is administered to a warm-blooded animal of about 70 kg is from about 200 mg to about 1200 mg.

The following Examples illustrate the present invention without in any way restricting the scope thereof. Temperatures are quoted in degrees celsuis.

EXAMPLE 1

A solution of 12.8 g (19.1 mmol) of N-{3-3-(4-acetyl-3-hydroxy-2-n-propylphenoxy)-2-hydroxypropoxy]-4-bromo-6-methylphenyl}-1-(4-methoxybenzyl)-tetrazole-5-carboxamide in 250 ml of trifluoroacetic acid and 25 ml of anisole is heated at reflux temperature for 30 minutes. The reaction mixture is concentrated under reduced pressure, 300 ml of ether and 400 ml of petroleum ether are added to the residue, and the crystals are filtered off. The N-{3-[3-(4-acetyl-3-hydroxy-2-n-propylphenoxy)-2-hydroxypropoxy]-4-bromo-6- methylphenyl}-1H-tetrazole-5-carboxamide thus obtained of melting point 155°–158°, 1H-NMR spectrum (δ against TMS, DMSO-d$_6$): 0.85 (triplet, 3H); 1.45 (multiplet, 2H); 2.25 (singlet, 3H); 2.55 (multiplet, 2H); 2.60 (singlet, 3H); 4.0–4.7 (multiplet, 4H); 5.90 (multiplet, 1H); 6.65 (doublet, 1H); 7.30 (singlet, 1H); 7.55 (singlet, 1H); 7.85 (doublet, 1H), 10.75 (singlet, 1H) 12.80 (singlet, 1H); is dissolved in 100 ml of acetone, and one equivalent of triethanolamine in 10 ml of acetone is added. Crystallisation sets in after ether has been added. This gives the triethanol ammonium salt of N-{3-[3-(4-acetyl-3-hydroxy-2-n-propylphenoxy)2-hydroxypropoxy]-4-bromo-6-methylphenyl}-1H-tetrazole-5-carboxamide of melting point 76° (decomposition).

N-{-[3-(4-acetyl-3-hydroxy-2-n-propylphenoxy)-2-hydroxypropoxy]-4-chloro-6-methylphenyl}-1H-tetrazole-5-carboxamide, an oil; 1H-NMR spectrum (δ against TMS, DMSO-d$_6$): 0.85 (triplet, 3H); 1.45 (multiplet, 2H); 2.25 (singlet, 3H); 2.55 (multiplet, 2H); 2.60 (singlet, 3H); 4.0–4.7 (multiplet, 4H); 5.90 (multiplet, 1H); 6.65 (doublet, 1H); 7.25 (singlet, 1H); 7.35 (singlet, 1H); 7.85 (doublet, 1H), 10.70 (singlet, 1H) 12.80 (singlet, 1H); and the triethanolammonium salt thereof are obtained analogously starting from N-{3-[3-(4-acetyl-3-hydroxy-2-n-propylphenoxy)-2-hydroxypropoxy]-4-chloro-6-methylphenyl}-1-(4-methoxybenzyl)-tetrazole-5-carboxamide.

The starting material can be prepared, for example, as follows:

0.32 g (7.4 mmol) of a 55% dispersion of sodium hydride in oil is added to a solution of 16.2 g (70 mmol) of 2-bromo-4-methyl-5-nitrophenol in 130 ml of ethanol. A solution of 18.4 g (73.5 mmol) of 4-(2,3-epoxypropoxy)-2-hydroxy-3-propylacetophenone in 150 ml of ethanol is then added dropwise, under reflux, in the course of two hours. The mixture is then heated at reflux temperature for a further eight hours. The reaction mixture is cooled, concentrated in vacuo to approx. 100 ml and poured onto ice. The aqueous phase is acidified with dilute hydrochloric acid and is extracted three times with methylene dichloride. The combined organic phases are washed with water, dried over sodium sulfate and evaporated in vacuo. Crystallisation from ether gives 3-[3-(4-acetyl-3-hydroxy-2-n-propylphenoxy)-2-hydroxypropoxy]-4-bromo-6-methylnitrobenzene of melting point 104°–106°.

3-[3-(4-acetyl-3-hydroxy-2-n-propylphenoxy)-2-hydroxypropoxy]-4-chloro-6-methylnitrobenzene of melting point 103°–105° C. is obtained analogously (starting from 2-chloro-4-methyl-5-nitrophenol).

2.0 g of Raney nickel are added to a solution of 23.3 g (48.3 mmol) of 3-[3-(4-acetyl-3-hydroxy-2-n-propylphenoxy)-2-hydroxypropoxy]-4-bromo-6-methylnitrobenzene in 240 ml of tetrahydrofuran, and hydrogenation is carried out at room temperature. The catalyst is filtered off and washed with tetrahydrofuran. The combined filtrates ar concentrated in vacuo, ether is added to the residue, and the precipitated crystals are filtered off. This gives 3-[3-(4-acetyl-3-hydroxy-2-n-propylphenoxy)-2-hydroxypropoxy]-4-bromo-6-methylaniline of melting point 78°–80° C.

3-[3-(4-acetyl-3-hydroxy-2-n-propylphenoxy)-2-hydroxypropoxy]-4-chloro-6-methylaniline of melting point 94°–95° is obtained analogously starting from 3-[3-(4-acetyl-3-hydroxy-2-n-propylphenoxy)-2-hydroxypropoxy]-4-chloro-6-methylnitrobenzene.

3.38 ml (38.8 mmol) of oxalyl chloride are added at 0°–5° to a suspension of 10.6 g (38.8 mmol) of potassium [1-(4-methoxybenzyl)-tetrazole]-5-carboxylate in 170 ml of benzene and 1.5 ml of pyridine, and the mixture is stirred at room temperature for 30 minutes. The reaction mixture is concentrated under reduced pressure and the residue is taken up in benzene and again evaporated under reduced pressure. The residue is dissolved in 135 ml of methylene dichloride, and the solution is added dropwise, at 0°–5° and in the course of 10 minutes, to a solution of 12.85 g (28.4 mmol) of 3-[3-(4-acetyl-3-hydroxy-2-n-propylphenoxy)-2hydroxypropoxy]-4-bromo-6-methylaniline and 2.7 ml (33 mmol) of pyridine in 100 ml of methylene dichloride. The mixture is then stirred for 3 hours at room temperature. The reaction mixture is diluted with methylene dichloride and is washed three times with water. The organic phase is dried over sodium sulfate and evaporated under reduced pressure The residue is filtered through 400 g of silica gel using 6:1 methylene dichloride/ethyl acetate. The eluate is evaporated and the residue is crystallised from ethanol. This gives N-{3-[3-(4-acetyl-3-hydroxy-2-n-propylphenoxy)-2-hydroxypropoxy]-4-bromo-6-methylphenyl}-1-(4-methoxybenzyl)-tetrazole-5-carboxamide of melting point 114°–116°.

N-{3-[3-(4-acetyl-3-hydroxy-2-n-propylphenoxy)-2hydroxypropoxy]-4-chloro-6-methylphenyl}-1-(4-methoxybenzyl)-tetrazole-5-carboxamide is obtained analogously starting from 3-[3-(4-acetyl-3-hydroxy-2-n-propylphenoxy)-2-hydroxypropoxy]-4-chloro-6-methylaniline.

EXAMPLE 2

A solution of 7.1 g (11.8 mmol) of N-{3-[3-(4-acetyl-3-hydroxy-2-n-propylphenoxy)-2-hydroxypropoxy]-2-cyanophenyl}-1-(4-methoxybenzyl)tetrazole-5-carboxamide in 150 ml of trifluoroacetic acid and 15 ml of anisole is heated at reflux temperature for 30 minutes. The reaction mixture is concentrated under reduced pressure, about 200 ml of ether and 300 ml of petroleum ether are added to the residue, and the crystals are filtered off. The N-{3-[3-(4-acetyl-3-hydroxy-2-n-propylphenoxy)-2-hydroxypropoxy]-2-cyanophenyl}-1H-tetrazole-5-carboxamide of melting point 210°–213° thus obtained is dissolved in 50 ml of hot acetone, and one equivalent of triethanolamine in 20 ml of acetone is added. Crystallisation sets in after ether has been added. This gives the triethanolammonium salt of N-{3-[3-(4-acetyl-3-hydroxy-2-n-propylphenoxy)-2-hydroxypropoxy]-2-cyanophenyl}-1H-tetrazole-5-carboxamide of melting point 80°–82°.

The starting materials are obtained, for example, as follows:

30 drops of Triton B are added to a solution of 34 g (0.207 mol) of 2-hydroxy-6-nitrobenzonitrile and 60 g of 4-[(2,3-epoxy)propoxy]-2-hydroxy-3-propylacetophenone in 450 ml of dimethylformamide. The solution is heated at reflux temperature for 1.5 hours and is freed from the solvent and the residue is taken up in 500 ml of ethyl acetate. After being washed with 500 ml of 0.5 N sodium hydroxide solution and with 500 ml of water, the solution is dried over magnesium sulfate. The solvent is removed by evaporation and the residue is chromatographed over silica gel using 95:5 methylene chloride/ethyl acetate. This gives 2-[3-(4-acetyl-3-hydroxy-2-propylphenoxy)-2-hydroxypropoxy]-6-nitrobenzonitrile of melting point 117°–119°.

2.5 g of 10% palladium-on-charcoal are added to a solution of 10 g (24.2 mmol) of 2-[3-(4-acetyl-3-hydroxy-2-propylphenoxy)-2-hydroxypropoxy]-6- nitrobenzonitrile and 10 g of cyclohexene in 500 ml of ethanol, and the mixture is heated at reflux temperature for 30 minutes. After cooling to room temperature, the mixture is filtered and the solvent is removed by evaporation. Ether is added to the residue, and the precipitated crystals are filtered off. This gives 3-[3-(4-acetyl-3-hydroxy-2-n-propylphenoxy)-2-hydroxypropoxy]-2-cyanoaniline of melting point 123°–125° C.

1.84 ml (21.5 mmol) of oxalyl chloride are added at 0°–5° to a suspension of 5.8 g (21.5 mmol) of potassium {1-(4-methoxybenzyl)-tetrazole}-5-carboxylate in 110 ml of benzene and 1.0 ml of pyridine, and the mixture is stirred for 30 minutes at room temperature. The reaction mixture is concentrated under reduced pressure and the residue is taken up in benzene and again evaporated under reduced pressure. The residue is dissolved in 80 ml of methylene chloride and is added dropwise, at 0°–5° and in the course of about 10 minutes, to a solution of 5.87 g (17.2 mmol) of 3-[3-(4-acetyl-3-hydroxy-2-n-propylphenoxy)-2-hydroxypropoxy]-2-cyanoaniline and 1.72 ml (21.5 mmol) of pyridine in 40 ml of methylene chloride. The mixture is then stirred at room temperature for 3 hours. The reaction mixture is diluted with methylene chloride and washed three times with water. The organic phases are combined, dried over sodium sulfate and evaporated under reduced pressure. The residue is chromatographed over silica gel using 6:1 methylene chloride/ethyl acetate. N-{3-[3-(4-acetyl-3-hydroxy-2-n-propylphenoxy)-2-hydroxypropoxy]-2-cyanophenyl}-1-(4-methoxybenzyl)tetrazole-5-carboxamide is obtained as a colourless oil.

EXAMPLE 3

Starting from 2-fluoro-4-methyl-5-nitrophenol, 4-methyl-5-nitrophenol and 2-hydroxy-5-methyl-4-nitrobenzonitrile, N-{3-[3-(4-acetyl-3-hydroxy-2-n-propylphenoxy)-2-hydroxypropoxy]-4-fluoro-6-methylphenyl}-1H-tetrazole-5-carboxamide, 1H-NMR spectrum ($\delta$ against TMS, DMSO-$d_6$): 0.85 (triplet, 3H); 1.45 (multiplet, 2H); 2.25 (singlet, 3H); 2.55 (multiplet, 2H); 2.60 (singlet, 3H); 4.0–4.7 (multiplet, 4H); 5.90 (multiplet, 1H); 6.65 (doublet, 1H); 7.25 (singlet, 1H); 7.65 (singlet, 1H); 7.85 (doublet, 1H), 10.70 (singlet, 1H) 12.80 (singlet, 1H); and its triethanolammonium salt, N-{3-[3-(4-acetyl-3-hydroxy-2-n-propylphenoxy)-2-hydroxypropoxy]-6-methylphenyl}-1H-tetrazole-5-carboxamide, 1H-NMR spectrum ($\delta$ against TMS, DMSO-$d_6$): 0.85 (triplet, 3H); 1.45 (multiplet, 2H); 2.25 (singlet, 3H); 2.55 (multiplet, 2H); 2.60 (singlet, 3H); 4.0–4.7 (multiplet, 4H); 5.90 (multiplet, 1H); 6.60 (multiplet, 2H); 7.10 (doublet, 1H); 7.80 (multiplet, 2H);10.70 (singlet, 1H) 12.80 (singlet, 1H); and its triethanolammonium salt and N-{3-[3-(4-acetyl-3-hydroxy-2-n-propylphenoxy)-2-hydroxypropoxy]-4-cyano-6-methylphenyl-1H-tetrazole-5-carboxamide, 1H-NMR spectrum ($\delta$ against TMS, DMSO-$d_6$): 0.85 (triplet, 3H); 1.45 (multiplet, 2H); 2.25 (singlet, 3H); 2.55 (multiplet, 2H); 2.60 (singlet, 3H); 4.0–4.7 (multiplet, 4H); 5.90 (multiplet, 1H); 6.65 (doublet, 1H); 7.30 (singlet, 1H); 7.45 (singlet, 1H); 7.85 (doublet, 1H), 10.70 (singlet, 1H) 12.80 (singlet 1H); and its triethanolammonium salt, respectively, are obtained in a manner analogous to that described in Example 1 or 2.

EXAMPLE 4

4.9 g of N-{3-[3-(4-acetyl-3-hydroxy-2-n-propylphenoxy)-2-hydroxypropoxy]-6-methylphenyl}-1H-tetrazole-5-carboxamide are dissolved in 45 ml of acetone, and a solution of 1.0 g of diethanolamine in 5 ml of acetone is added. Crystallisation sets in after diethyl ether has been added. The mixture is allowed to stand for 30 minutes at 5°–10° and the crystals are filtered off with suction, rinsed with diethyl ether and allowed to dry in the air. This gives the diethanolammonium salt of N-{3-[3-(4-acetyl-3-hydroxy-2-n-propyl)-phenoxy)-2-hydroxypropoxy]-6-methylphenyl}-1H-tetrazole-5-carboxamide. The sodium, potassium, diethylammonium and tris-(hydroxymethyl)-methylammonium salt of this compound can also be prepared analogously.

The sodium, potassium, diethanolammonium, diethylammonium and tris-(hydroxymethyl)-methylammonium salt of N-{3-[3-(4-acetyl-3-hydroxy-2-n-propylphenoxy)-2-hydroxypropoxy]-2-cyanophenyl}-1H-tetrazole-5-carboxamide, N-{3-[3-(4-acetyl-3-hydroxy-2-n-propylphenoxy)-2-hydroxypropoxy]4-bromo-6-methylphenyl}-1H-tetrazole-5-carboxamide, N-{3-[3-(4-acetyl-3-hydroxy-2-n-propylphenoxy)-2-hydroxypropoxy]-4-chloro-6-methylphenyl}-1H-tetrazole-5-carboxamide, N-{3-[3-(4-acetyl-3-hydroxy-2-n-propylphenoxy)-2-hydroxypropoxy]-4-fluoro-6-methylphenyl}-1H-tetrazole-5-carboxamide and N-{3-[3-(4-acetyl-3-hydroxy-2-n-propylphenoxy)-2-hydroxypropoxy]-4-cyano-6-methylphenyl}-1H-tetrazole-5-carboxamide are also obtained analogously in each case.

EXAMPLE 5

Tablets containing 25 mg of active compound, for example the triethanolammonium salt of N-{3-[3-(4-acetyl-3-hydroxy-2-propylphenoxy)-2-hydroxypropoxy]-4-bromo-6-methylphenyl}-1H-tetrazole-5-carboxamide, can be prepared in the following way:

| Ingredients (for 1000 tablets): | |
|---|---|
| Active compound | 25.0 g |
| Lactose | 100.7 g |
| Wheat starch | 7.5 g |
| Polyethylene glycol 6000 | 5.0 g |
| Talc | 5.0 g |
| Magnesium stearate | 1.8 g |
| Deionised water | q.s. |

Preparation:

All the solid ingredients are first forced through a sieve of mesh width 0.6 mm. The active compound, the lactose, the talc, the magnesium stearate and half of the starch are then mixed. The other half of the starch is suspended in 40 ml of water, and this suspension is added to a boiling solution of the polyethylene glycol in 100 ml of water, and the mixture is granulated, if necessary with the addition of water. The granules are dried overnight at 35°, forced through a sieve of mesh width 1.2 mm and compressed to give tablets, concave on both sides, of diameter about 6 mm.

Tablets containing in each case 25 mg of another of the compounds of the formula I mentioned in Examples 1 to 4 can also be prepared analogously.

EXAMPLE 6

Tablets for chewing, containing 30 mg of active compound, for example the triethanolammonium salts of N-{3-[3-(4-acetyl-3-hydroxy-2-propylphenoxy)-2-hydroxypropoxy]-4-bromo-6-methylphenyl}-1H-tetrazole-5-carboxamide, can be prepared, for example, as follows:

| Composition (for 1000 tablets): | |
|---|---|
| Active compound | 30.0 g |
| Mannitol | 267.0 g |
| Lactose | 179.5 g |
| Talc | 20.0 g |
| Glycine | 12.5 g |
| Stearic acid | 10.0 g |
| Saccharin | 1.0 g |
| 5% gelatine solution | q.s. |

Preparation:
All the solid ingredients are first forced through a sieve of mesh width 0.25 mm. The mannitol and the lactose are mixed, granulated with the addition of gelatine solution, forced through a sieve of mesh width 2 mm, dried at 50° and again forced through a sieve of mesh width 1.7 mm. The active compound, the glycine and the saccharin are mixed carefully, the mannitol, the lactose granules, the stearic acid and the talc are added, and the whole is thoroughly mixed and compressed to give tablets, concave on both sides, of diameter about 10 mm and having a score on the upper side.

Tablets containing in each case 30 mg of another of the compounds of the formula I mentioned in Examples 1 to 4 can also be prepared analogously.

EXAMPLE 7

Tablets containing 100 mg of active compound, for example the triethanolammonium salt of N-{3-[3-(4-acetyl-3-hydroxy-2-propylphenoxy)-2-hydroxypropoxy]-4-bromo-6-methylphenyl}-1H-tetrazole-5-carboxamide, can be prepared as follows:

| Composition (for 1000 tablets): | |
|---|---|
| Active compound | 100.0 g |
| Lactose | 248.5 g |
| Maize starch | 17.5 g |
| Polyethylene glycol 6000 | 5.0 g |
| Talc | 15.0 g |
| Magnesium stearate | 4.0 g |
| Deionised water | q.s. |

Preparation:
The solid ingredients are first forced through a sieve of mesh width 0.6 mm. The active compound, lactose, talc, magnesium stearate and half of the starch are then intimately mixed. The other half of the starch is suspended in 65 ml of water, and this suspension is added to a boiling solution of the polyethylene glycol in 260 ml of water. The resulting paste is added to the pulverulent substances, and the whole is mixed and granulated, if necessary with the addition of water. The granules are dried overnight at 35°, forced through a sieve of mesh width 1.2 mm and compressed to give tablets, concave on both sides, of diameter about 10 mm and having a breaking notch on the upper side.

Tablets containing 100 mg of another compound of the formula I according to Examples 1 to 4 can also be prepared analogously.

EXAMPLE 8

An inhalation suspension containing a propellant and forming a solid aerosol and containing 0.1% by weight of N-{3-[3-(4-acetyl-3-hydroxy-2-propylphenoxy)-2-hydroxypropoxy]-4-bromo-6-methylphenyl}-1H-tetrazole-5-carboxamide (active compound) can be prepared, for example, as follows:

| Composition: | |
|---|---|
| Active compound micronised | 0.1% by weight |
| "Sorbitan trioleate" | 0.5% by weight |
| Propellant A (trichlorotrifluoroethane) | 4.4% by weight |
| Propellant B (mixture of 15 parts of dichlorodifluoromethane and 80 parts of symmetrical dichlorotetrafluoroethane) | q.s. |

Preparation:
The active compound is suspended, with the exclusion of moisture, in the trichlorotrifluoroethane by means of a convntional homogeniser, with the addition of the sorbitan trioleate, the suspension is run into a dosing aerosol container, and the latter is closed and filled under pressure with the dichlorodifluoromethane/dichlorotetrafluoroethane mixture.

Inhalation suspensions containing another compound of the formula I according to Examples 1 to 4 can also be prepared analogously.

EXAMPLE 9

An approximately 2% aqueous solution, suitable for inhalation, of the triethanolammonium salt of N-{3-[3-(4-acetyl-3-hydroxy-2-propylphenoxy)-2-hydroxypropoxy]-4-bromo-6-methylphenyl}-1H-tetrazole-5-carboxamide as the active compound can be prepared, for example, in the following composition:

| Composition | |
|---|---|
| Active compound | 2000 mg |
| Stabiliser, for example disodium ethylenediaminetetraacetate | 10 mg |
| Preservative, for example benzalkonium chloride | 10 mg |
| Water, freshly distilled | ad 100 ml |

Preparation:
The active compound is dissolved in freshly distilled water. The stabiliser and the preservative are then added. After all the components have dissolved completely, the resulting solution is made up to 100 ml and run into phials, and the latter are closed so as to be gas tight.

2% inhalation solutions containing another active compound from one of Examples 1 to 4 can also be prepared analogously.

EXAMPLE 10

Capsules suitable for insufflation and containing about 25 mg of the triethanolammonium salt of N-{3-[3-14-acetyl-3-hydroxy-2-propylphenoxy)-2-hydroxypropoxy]-4-bromo-6-methylphenyl}-1H-tetrazole-5-carboxamide as the active compound can be prepared, for example, in the following composition:

| Composition | |
|---|---|
| Active compound | 25 g |
| Lactose, finely ground | 25 g |

Preparation:
The active compound and the lactose are intimately mixed. The resulting powder is then sieved and filled in portions of 50 mg each into 1000 gelatine capsules.

Insuffation capsules containing in each case an active compound according to one of Examples 1 to 4 can also be prepared analogously.

What is claimed is:

1. A compound of the formula

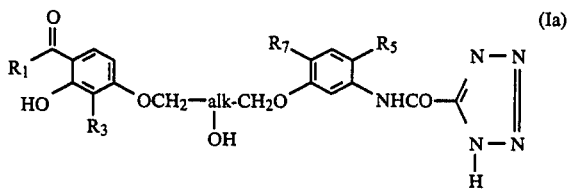

in which
R₁ is lower alkyl having not more than 4 C atoms;
R₃, is linear lower alkyl having not more than 4 C atoms; and
 (a) R₅ is lower alkyl, R₆ is hydrogen, and R₇ is hydrogen, halogen of atomic number not greater than 35 or cyano; or
 (b) R₅ is hydrogen, R₆ is cyano, and R₇ is hydrogen; and
alk is terminally attached methylene or ethylene, or a pharmaceutically acceptable salt thereof.

2. A compound as claimed in claim 1 being N-{3-[3-(4-acetyl-3-hydroxy-2-n-propylphenoxy)-2-hydroxypropoxy]-4-bromo-6-methylphenyl}-1H-tetrazole-5-carboxamide or a pharmaceutically acceptable salt thereof.

3. A compound as claimed in claim 1 being N-{3-[3-(4-acetyl-3-hydroxy-2-n-propylphenoxy)-2-hydroxypropoxy]-2-cyanophenyl}-1H-tetrazole-5-carboxamide or a pharmaceutically acceptable salt thereof.

4. A compound as claimed in claim 1 being N-{3-[3-(4-acetyl-3-hydroxy-2-n-propylphenoxy)-2-hydroxypropoxy]-6-methylphenyl}-1H-tetrazole-5-carboxamide or a pharmaceutcally acceptable salt thereof.

5. A compound as claimed in claim 1 being N-{3-[3-(4-acetyl-3-hydroxy-2-n-propylphenoxy)-2-hydroxypropoxy]-4-fluoro-6-methylphenyl}-1H-tetrazole-5-carboxamide or a pharmaceutically acceptable salt thereof.

6. A compound as claimed in claim 1 being N-{3-[3-(4-acetyl-3-hydroxy-2-n-propylphenoxy)-2-hydroxypropoxy]-4-fluoro-6-methylphenyl}-1H-tetrazole-5-carboxamide or a salt thereof.

7. A compound as claimed in claim 1 being N-{3-[3-(4-acetyl-3-hydroxy-2-n-propylphenoxy)-2-hydroxypropoxy]-4-cyano-6-methylphenyl}-1H-tetrazole-5-carboxamide or a pharmaceutically acceptable salt thereof.

8. The pharmaceutically acceptable salt of a compound according to claim 7 which is the sodium, triethanolammonium, diethylammonium, diethanolammonium, or tris-(hydroxymethyl)-methylammonium salt.

9. An antiallergic pharmaceutical formulation containing a therapeutically effective amount of a compound according to claim 1 together with pharmaceutically acceptable adjuncts and excipients.

10. A method of treatment of allergies in a mammal in need of the same, which comprises administering to said mammal an effective antiallergic amount of a compound or pharmaceutically acceptable salt according to claim 1.

* * * * *